United States Patent [19]

Artusi

[11] Patent Number: 4,535,890
[45] Date of Patent: Aug. 20, 1985

[54] CONTAINER WHICH IS A FORM OF PACKAGING IN PARTICULAR FOR MEDICAMENTS AND THE LIKE AND PROCESS FOR ITS MANUFACTURE

[75] Inventor: Aldo Artusi, Schaffhausen, Switzerland

[73] Assignee: Medipack AG, Schaffhausen, Switzerland

[21] Appl. No.: 487,104

[22] Filed: Apr. 21, 1983

Related U.S. Application Data

[63] Continuation of Ser. No. 219,500, Dec. 23, 1980, abandoned.

[30] Foreign Application Priority Data

Dec. 28, 1979 [DE] Fed. Rep. of Germany ....... 2952616

[51] Int. Cl.³ ..................... B65D 83/04; B65D 85/42
[52] U.S. Cl. .................................. 206/530; 206/552; 206/539; 206/540; 206/468; 220/346; 229/43
[58] Field of Search ............... 206/530, 532, 539, 540, 206/468; 220/345, 346, 351; 229/43

[56] References Cited

U.S. PATENT DOCUMENTS

| | | | |
|---|---|---|---|
| 3,464,544 | 9/1969 | Franck | 206/468 |
| 3,812,963 | 5/1974 | Zamuranec et al. | 206/468 |
| 3,854,649 | 12/1974 | Wagner et al. | 206/468 |
| 3,876,133 | 4/1975 | Smith | 220/346 |
| 4,192,422 | 3/1980 | Kotyuk | 206/468 |
| 4,223,788 | 9/1980 | Jaeger et al. | 220/346 |
| 4,272,010 | 6/1981 | Capo | 229/43 |

Primary Examiner—Joseph Man-Fu Moy

[57] ABSTRACT

A container in the form of a packaging having at least one supporting or receptacle part such as for medicaments or the like, which if necessary or desired are contained in a separate medicament vessel and a lid which is slidable on guiding strips on the receptacle part. The slidable engagement of the lid and receptacle is effected by longitudinal edge portions on the lid or receptacle engaging in grooves on the other part. At opposite ends of the container, flaps made at least in part of flexible or reversible material are provided and, when the container is closed serve as stops which restrict relative movement between the lid and the receptacle. The flaps may be bendable, or removable or contain projections which may engage in recesses when the container is closed. In a process for the manufacture of such a container, the part with the grooves is made of a material with a lower softening point than the material of the other part and after the lid is placed on the receptacle, the material is brought to softening condition and bent around the guiding edges to form the grooves.

9 Claims, 6 Drawing Figures

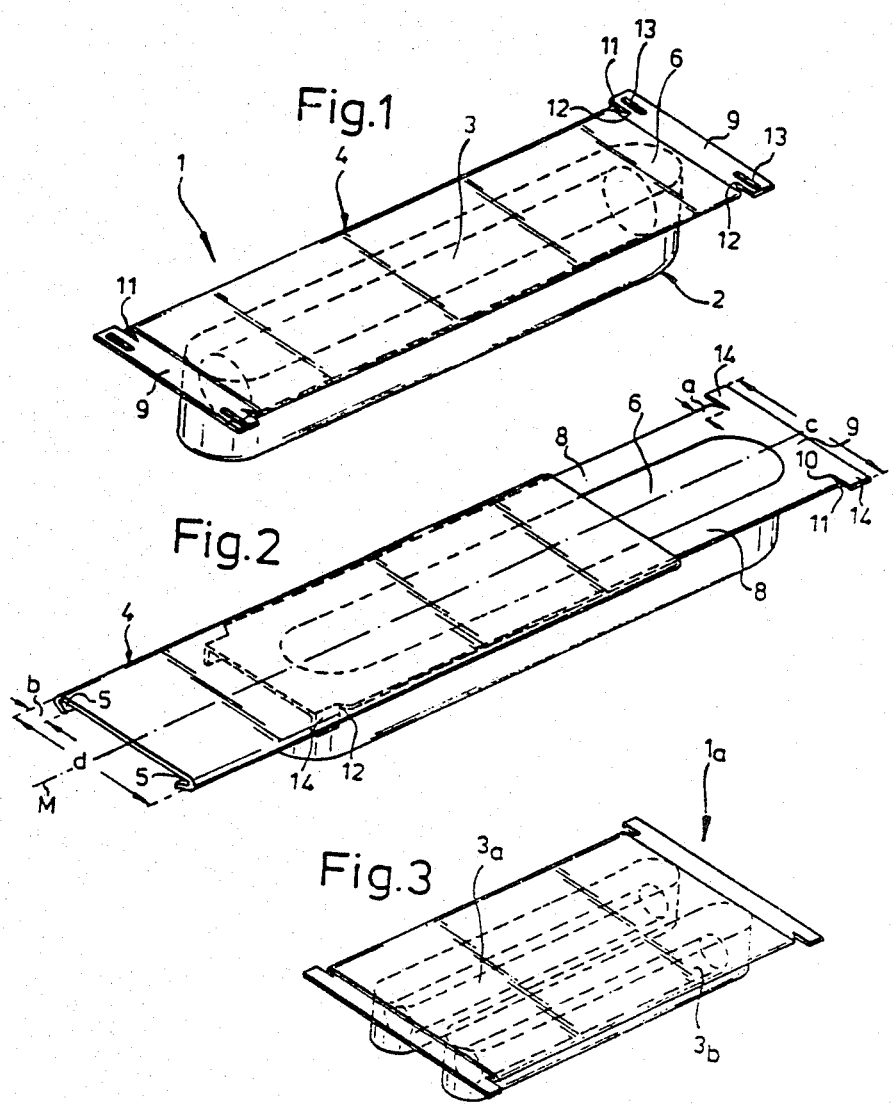

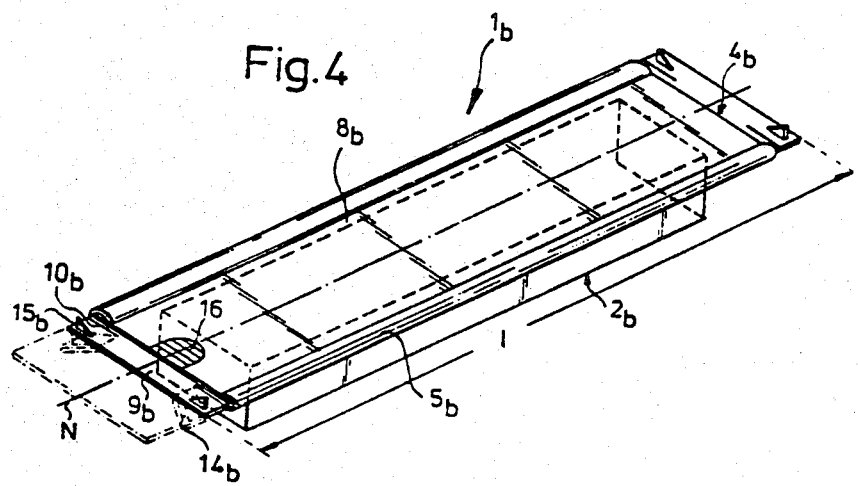
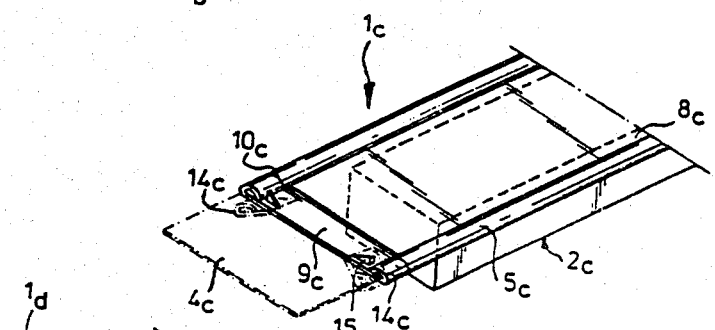
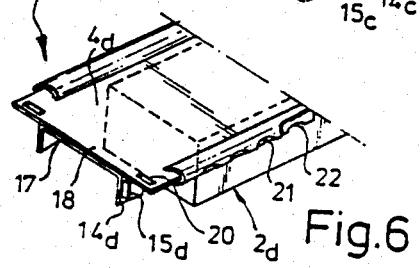

CONTAINER WHICH IS A FORM OF PACKAGING IN PARTICULAR FOR MEDICAMENTS AND THE LIKE AND PROCESS FOR ITS MANUFACTURE

This application is a continuation of application Ser. No. 219,500, filed Dec. 23, 1980 now abandoned.

BACKGROUND OF THE INVENTION (a) Field of the Invention

The invention relates to a container which is in the form of a packaging having at least one supporting or receptacle part for contents, in particular for its medicaments or the like which, if necessary, are contained in respective vessels. The invention further relates to a lid which is slidable on guiding strips which are provided at the sides of the receptacle part and engage in channels on the lid.

The invention also relates to a process for the manufacture of the container.

(b) Prior Art

Packaging for medicaments is known in which a flat lid lying on the container engages two, flat, opposite sides of the container such that the lid and the bottom part are slidable with respect to each other.

One of the basic disadvantages of this known packaging is that it is not child-proof. To open it and gain access to the medicine, a child need only have the ability to complete one single movement viz., the sliding of the lid and the lower part with respect to each other.

By definition, a packaging is considered to be child-proof only if at least two different manipulations are required to open it.

The known packaging does not exhibit this feature, or is so complicated and expensive to make and use that its sales and application is restricted.

SUMMARY OF THE INVENTION

In view of this, it is therefore an object of the invention to provide a packaging of the above mentioned kind which is child-proof and is easy and inexpensive to manufacture.

This object is achieved in accordance with the invention in that on opposite sides of the receptacle part or lid flaps are provided, and are made, at least in part, of flexible or reversible material and, then the container is closed, serve as stops which restrict the relative movement of the lid and receptacle part of the packaging.

The invention embraces also, however, a container as a form of packaging in which the flaps of the above mentioned kind are provided on the opposite sides of the receptacle part and the lid.

The packaging then comprises, preferably, a drawn receptacle part and lid, with the grooves for the guiding strips on the long sides and the flaps at the ends. This form of packaging has the advantage that, in order to open it, two different types of manipulation are required by human hands, and that these must be carried out simultaneously so that two hands are required. One hand removes the restriction to the relative movement of lid and receptacle part provided by the flaps, and the other effects this relative movement which comprises sliding the lid on the receptacle part along the grooves at the side engaging the guiding strips.

A child is not able to carry out these movements simultaneously, which makes the packaging child-proof and particularly suitable for containing medicaments or vessels holding medicaments.

By manufacturing the flaps from flexible or reversible material the container can be re-used. Also, the user is not required to make any additional manipulations to be able to close the packaging; this closes itself on returning the lid to the closed position.

In the simplest case, the closure is effected by the flaps being of a length which is larger than the breadth of the lid and/or the receptacle part. If, in this case, the user wishes to displace the lid by sliding, he pushes against the flaps and is not able to overcome this obstacle without a second manipulation viz., bending over the flaps. It is then, according to the invention, of no consequence whether the guiding grooves are on the receptacle part or the lid, and likewise whether the flap projects from the receptacle or the lid. In both cases it fulfills the function of restricting the movement.

In order to simplify the handling, the invention gives preference to providing a slit between the flap and the receptacle or lid, the depth of which is at least equal to the depth of the groove. This enables the flap to be bent back so far that the lid, even when it itself carries the edge grooves, can be pushed away without difficulty, over the flap.

A strengthening rib helps to make the end pieces more reversible.

Projections on the end pieces provide the packing with an even greater degree of safety. They prevent the lid from sliding over the flaps. This obstacle is also overcome by bending down the end pieces on the flaps.

In a container which includes mating flaps on the lid and on the receptacle part, it has been found advantageous to provide on one flap projections which engage in openings in the other flap. It is then sufficient when one flap is bent back on opening the container. When manufacturing the container with contents, or after filling the container, it is preferably provided with a seal on or in the slits. An unbroken seal then provides an indication that the packaging has not been opened.

The design of this form of packaging is simple in concept, but effective, and very inexpensive to manufacture.

A method for manufacturing the above described packaging is preferably such that the lid, made of a material with a lower softening point than that used for the receptacle part, is laid on the receptacle part, brought to a softened state and then bent to form the grooves around the guiding strips.

According to this method, the receptacle part is formed in a first step and the covering carried out in a second step, which, compared with the known process, represents a savings of one operation viz., the pushing together of a separately manufactured receptacle and lid.

Furthermore, this process makes it possible to obtain a seal between the flap and receptacle or lid in the slits, without requiring a special operation for this. This sealing is carried out during the manufacture of the receptacle or the lying down of the piece for the lid.

The material for the lid and/or the receptacle part are preferably plastics with different softening points, and these can preferably be cut to size or likewise removed from a roll of material.

BRIEF DESCRIPTION OF THE FIGURES OF THE DRAWINGS

FIG. 1 is a perspective view of a closed packaging container according to the invention.

FIG. 2 is a perspective view of a packaging container opened to about a half-way position.

FIG. 3 is a perspective view of a packaging similar to FIG. 1, having two container compartments.

FIG. 4 is a perspective view of a further embodiment of a packaging similar to FIG. 1.

FIG. 5 is a perspective view of another embodiment of packaging similar to FIG. 1.

FIG. 6 is a perspective view of a further embodiment of a packaging container according to the invention.

DETAILED DESCRIPTION

A container or packaging 1 according to FIG. 1, comprises a receptacle part 2 for medicaments, i.e. a medicament capsule 3 or the like and a rectangular lid 4.

Both long sides of the lid 4 are bent at the edges towards the central axis M of the lid 4 such that, as can be seen in FIG. 2, two grooves 5 are formed. Receptacle part 2 comprises a rectangular sheet 8, the contour of which corresponds approximately to that of the lid 4, and in which an opening 6 is provided. Extending from the opening 6 is a single cavity in which the medicament or capsule 3 is placed.

Flaps 9 are formed on both short sides i.e. the ends of the sheet 8.

In the closed position, the lid 4 covers the opening 6 with the grooves 5 engaging both long sides of the sheet 8. At the same the lid 4 is restricted in movement by the flaps 9 of length c, which is larger than the breadth d of the lid 4. As a result of this construction the lid 4 is held in the closed position.

At the edge of the sheet 8, at the place of transition to flap 9 a blind slit 10 of length a is provided, equal at least to depth b of groove 5. As a result of this, end pieces 14 are created on the flap 9. The slit 10 is, if necessary or desired, provided with a seal 11 which must be broken the first time use is made of the packaging 1.

The flap 9, but in particular the end pieces, is made of flexible or reversible material.

To open the container 2, the end pieces 14 on the flaps 9 must be bent down (see dotted lines in FIG. 2) using two fingers of a person not shown; the lid 4 can then be pushed with the other hand over the flap 9. Tip 12 is the beginning of a buckling line crossing the flap 9.

In order to improve the reversibility of the material of the flap 9, a rib 13 is provided at the place where fracture should occur.

FIG. 3 shows a form of packaging 1a which corresponds to that in FIG. 1 but which accommodates two capsules or the like 3a and 3b of medicament. Also foreseen is to close off the opening 6 in an airtight manner by means of a foil, which is not shown here and which has to be removed the first time access is sought to the contents of the container 1.

FIGS. 4 and 5 show containers 1b and 1c respectively, the closure means of which are of different construction. Whereas in FIG. 1 the lid 4 is provided with the grooves 5 which engage sheet 8 of the receptacle 2, in the embodiments of the container 1b, 1c according to the invention shown in FIGS. 4 and 5, the lids 4b, 4c are each in the form of a simple rectangular sheet which is engaged in grooves 5b, 5c which are on the sheets 8b, 8c of the receptacle parts 2b, 2c by bending the edge regions towards the central axis N of the receptacle part 2.

At both ends of the sheets 8b, 8c, respective flaps 9b, 9c made of flexible, reversible material are provided. By providing slits 10b, 10c between the flaps 9b, 9c and sheets 8b, 8c end pieces 14b, 14c are produced, each of which is provided with a respective piece 15b, 15c.

Only after both end pieces 14b, 14c of a flap 9b, 9c with projections 15b, 15c have been bent down is the lid 4b, 4c made free and able to be displaced by sliding.

The embodiments according to FIGS. 4 and 5 differ in that in FIG. 5 a tongue 14c of the end piece 14 or 14b on the flap 9 is bent towards the central axis and thus forms a groove.

A depression means or the like 16 for obtaining a grip is provided on the lid 4b.

According to the embodiment shown in FIG. 6, respective flaps 18 17 are provided on lid 4d and receptacle part 2d and such that flap 17 carries projections 15d which, when the container 1d is closed, engages in openings 20 in flap 18. In this case too, in order to open the container, the end pieces 14d created by slits on flap 17 must be bent down so that the projections 15d are removed from the openings 20.

As shown in FIG. 6, the receptacle part 2d is provided with indentations 21 which are approximately in line with recesses 22 in the lid 4d. On sliding the lid 4d, these recesses 22 and indentations 21 match up, preferably after each tablet or the like is made accessible, so that the following tablet or the like remains protected.

What is claimed is:

1. A container comprising a receptacle part and a lid part, said receptacle part having a cavity for receiving stored contents in the container, said receptacle part and lid part including respective opposed portions one of which is in the form of a groove and the other of which is in the form of an edge portion slidably engaged in said groove to permit relative slidable movement of said lid part and receptacle part between open and closed positions, and displaceable flap means on one of said parts having a first position blocking relative movement of said lid and receptacle parts and a second displaced position in which relative slidable movement of said parts is permitted, said parts having longitudinal edges parallel to the direction of relative sliding movement of said parts and opposite transverse ends, said flap means comprising flaps located at both edges of each of said opposite ends to hold the lid part and receptacle part in said closed position, said one part being provided with slits each forming a respective flap, each slit extending transversely from a longitudinal edge of said one part, each slit having a length at least equal to the depth of said groove, each of said flaps including stop means for holding the lid part and receptacle part in said closed position by blocking relative movement of said parts.

2. A container as claimed in claim 1 wherein said flaps on said one part are bendable about longitudinal axes.

3. A container as claimed in claim 1 wherein said flaps are flexible and return to said first position from said displaced position when released from the latter.

4. A container as claimed in claim 1 wherein said longitudinal edges are longer than said ends.

5. A container as claimed in claim 1 wherein each said slit is closed by a seal.

6. A container as claimed in claim 1 comprising reinforcement ribs on said flaps.

7. A container as claimed in claim 1 wherein said flaps include parts extending laterally beyond said grooves to form said stop means.

8. A container as claimed in claim 1 wherein said stop means includes projections on said flaps, said one part being substantially planar and said projections extending from the plane of said one part.

9. A container as claimed in claim 1 wherein the other part is provided with openings positioned to receive said projections in the closed position of the container.

* * * * *